United States Patent
Sundermeyer et al.

(10) Patent No.: US 9,540,401 B2
(45) Date of Patent: Jan. 10, 2017

(54) METHOD FOR PRODUCING ALKYL-INDIUM COMPOUNDS AND THE USE THEREOF

(71) Applicant: UMICORE AG & CO. KG, Hanau-Wolfgang (DE)

(72) Inventors: Joerg Sundermeyer, Marburg (DE); Annika Frey, Hanau (DE); Wolf Schorn, Giessen (DE); David Grosse-Hagenbrock, Marburg (DE); Ralf Karch, Kleinostheim (DE); Andreas Rivas-Nass, Schriesheim (DE); Eileen Woerner, Nidderau (DE); Angelino Doppiu, Seligenstadt (DE)

(73) Assignee: UMICORE AG & CO. KG, Hanau-Wolfgang (DE)

( * ) Notice: Subject to any disclaimer, the term of this patent is extended or adjusted under 35 U.S.C. 154(b) by 0 days.

(21) Appl. No.: 14/913,026

(22) PCT Filed: Aug. 18, 2014

(86) PCT No.: PCT/EP2014/067546
§ 371 (c)(1),
(2) Date: Feb. 19, 2016

(87) PCT Pub. No.: WO2015/024893
PCT Pub. Date: Feb. 26, 2015

(65) Prior Publication Data
US 2016/0207941 A1 Jul. 21, 2016

(30) Foreign Application Priority Data

Aug. 22, 2013 (DE) .......................... 10 2013 216 637
Jul. 1, 2014 (DE) .......................... 10 2014 109 228

(51) Int. Cl.
*C07F 5/00* (2006.01)

(52) U.S. Cl.
CPC ...................... *C07F 5/00* (2013.01)

(58) Field of Classification Search
CPC ...................................................... C07F 5/00
USPC ......................................... 556/1; 427/255.28
See application file for complete search history.

(56) References Cited

U.S. PATENT DOCUMENTS

| | | |
|---|---|---|
| 4,847,399 A | 7/1989 | Hallock et al. |
| 5,380,895 A | 1/1995 | Krafft |
| 5,663,390 A | 9/1997 | Giolando |
| 8,513,447 B1 | 8/2013 | Maggiarosa et al. |
| 2014/0287141 A1* | 9/2014 | Karch ............... C23C 16/301 427/252 |

FOREIGN PATENT DOCUMENTS

| | | |
|---|---|---|
| DE | 37 42 525 A1 | 6/1989 |
| EP | 0 372 138 A1 | 12/1988 |
| KR | 101221861 B1 | 1/2013 |
| WO | 89/05303 A1 | 6/1989 |
| WO | 2015/024894 A1 | 2/2015 |

OTHER PUBLICATIONS

International Search Report for PCT/EP2014/067546, dated Nov. 10, 2014 in English and German Language.
Gynane, M. J. S, Waterworth, L. G. und Worrall, I. J., J. "Preliminary Communication: Formation of Methyl-and Ethylgallium Halides by the Direct Reaction Between the Metal and Alkyl Halide" Journal of Organometallic Chemistry, 40, 1972, C59-C60.
Gynane, M. J. S, Waterworth, L. G. und Worrall, I. J., J. "Preliminary Communication: The Synthesis of Lower Alkylindium Halides by the Direct Reaction Between the Metal and Alkyl Halides" Journal of Organometallic Chemistry, 40, 1972, C9-C10.
Bähr, Burba: Organo-Indium-Verbindungen. y: Houben-Weyl, 1970. 350.
Gynane, M. J. S, Waterworkth, L. G. und Worrall, I. J., J. "Oxidative Addition Reactions of Group III Metals in Low Oxidation States: III*. Reaction s of Indium Monohalides with Alkyl Halides" Journal of Organometallic Chemistry, 43, 1972, 257-264.
Schöllkopf: Li-organische Verbindungen, y: Houben-Weyl, 1970. 134.
Stoll S L, et al: "Selenide and Selenolate Compounds of Indium: A Comparative Study of In—Se Bond-Forming Reactions", Journal of the Chemical Society, Dalton Transactions, Chemical Society. Letchworth, GB, Jan. 1, 1997, pp. 1315-1321, SP001146779.
Konrad Koszinowski: "Oxidation State, Aggregation, and Heterolytic Dissociation of Allyl Indium Reagents", Journal of the American Chemical Society, vol. 132, No. 17, May 5, 2010, pp. 6032-6040, XP55151064.

* cited by examiner

*Primary Examiner* — Porfirio Nazario Gonzalez
(74) *Attorney, Agent, or Firm* — Smith, Gambrell & Russell, LLP

(57) ABSTRACT

The invention relates to a method for the cost-effective and environmentally friendly production of dialkyl indium chloride in high yield and with high selectivity and purity. The dialkyl indium chloride produced according to the invention is particularly suitable, also as a result of the high purity and yield, for the production, on demand, of indium-containing precursors in high yield and with high selectivity and purity. As a result of the high purity, the indium-containing precursors that can be produced are particularly suitable for metal organic chemical vapor deposition (MOCVD) or metal organic vapor phase epitaxy (MOVPE). The novel method according to the invention is characterized by the improved execution of the method, in particular a rapid process control. Owing to targeted and extensive use of raw materials that are cost-effective and have a low environmental impact, the method is also suitable for use on an industrial scale.

20 Claims, No Drawings

METHOD FOR PRODUCING ALKYL-INDIUM COMPOUNDS AND THE USE THEREOF

The invention provides a process for preparing dialkylindium chloride, characterized by the general formula $R_2InCl$ (also referred to hereinafter as compound (A)) in high yield and with high selectivity and purity.

The dialkylindium chloride prepared in accordance with the invention is particularly suitable, because of its high purity and yield as well, for preparation of indium-containing precursors in accordance with demand, preferably those of the general formula $R_3In$ (also referred to hereinafter as compound (B)) or $R_2InR'$ (also referred to hereinafter as compound (C)). The indium-containing precursors obtainable with high yield and in high purity from compound (A), because of their high purity, are particularly suitable for metal-organic chemical vapour deposition (MOCVD) or metal-organic chemical vapour phase epitaxy (MOVPE).

Where the term "process" is used in accordance with this invention, this always means the process for preparing the compound (A) and the optional process for preparing indium-containing precursors, preferably of the compounds (B) or (C), which follows on.

PRIOR ART

The prior art describes various processes for preparing compounds which are typically used as organometallic precursors for MOCVD processes, i.e. the starting materials thereof, referred to hereinafter in simplified form as "precursor starting material".

"Precursor starting materials" in the context of this invention are those which can be converted via further reaction steps to the actual organometallic precursors, which can then be used directly in MOCVD or MOVPE processes (referred to as "precursors" or "indium-containing precursors" for short). It is advantageous here to provide such precursor starting materials or precursors by those precursor starting materials which are themselves obtainable with high selectivity and yield. In addition, it can be very advantageous to provide precursor starting materials which are preparable in a simple manner and with high purity and may be isolable and of sufficient storage stability to enable very rapid preparation of high-purity precursors for MOCVD or MOVPE processes in accordance with demand. The MOCVD or MOVPE processes are especially used in the production of films for optoelectronic applications such as solar cells or LEDs, which typically requires ultra-high purity of the particular precursor used, and the absence or the presence of only very small proportions of oxygen-containing impurities.

For instance, there are various known processes for preparing, for example, indium-containing, gallium-containing or else aluminium-containing precursors or corresponding precursor starting materials. However, the respective process conditions are not necessarily transferable, or cannot be transferred unchanged. It should be taken into account that the elements aluminium, gallium and indium already exhibit different chemical behaviour, which regularly results in the need for a particular tailored process regime in production of respective precursors.

Processes known in the prior art for preparing indium-containing precursors or precursor starting materials often encounter considerable difficulties with regard to preparation in the purity and amount required for customary uses. For instance, the electrical properties of the semiconductor layers produced from indium-containing precursors by MOCVD or MOVPE can be considerably impaired by impurities in the precursors or precursors starting materials. Numerous preparation processes are additionally very time-consuming. In addition, frequently only low yields are achieved, and the reaction steps are frequently characterized by a reduced selectivity. Because of the use of organic solvents as well in known preparation processes for preparing indium-containing precursors or precursor starting materials, the processes are usually costly and not very environmentally friendly, and are usually associated with solvent residues in the intermediates and the end products, which in turn considerably restrict the use thereof or necessitate a costly and inconvenient purification.

DE 37 42 525 A1 relates to a process for preparing metal alkyls such as trimethylindium, and describes a preparation proceeding from lithium tetramethylindate as precursor starting material by reaction with indium trichloride in an organic solvent. A mixture comprising trimethylindium is obtained, and the latter subsequently still has to be isolated and purified. Even after purification, the yield is reported as only 82% of the theoretical value. The preparation is also characterized by a relatively high process duration of more than 24 hours.

EP 0 372 138 A1 describes a process for preparing organometallic compounds, by which trialkylindium compounds too are obtainable via a nonvolatile precursor starting material which may, for example, be lithium tetramethylindate. The preparation of lithium tetramethylindate from indium trichloride takes place in diethyl ether with addition of methyllithium, which makes the process very costly overall. The lithium tetramethylindate is reacted with indium trichloride to give trimethylindium, which subsequently still has to be purified. No figures are given for the actual yield. Moreover, the process described is very costly and inconvenient, one reason being the numerous isolation and purification steps.

Gynane et. al. describe the reaction of indium with alkyl bromides and alkyl iodides to give sesquihalides (Gynane, M. J. S., Waterworth, L. G. and Worrall, I. J., J. Organometal. Chem., 40, 1972). A further publication also describes the reaction of indium monobromide or indium monoiodide with alkyl iodides or alkyl bromides to give alkylindium dihalides, but very long reaction times are required (Gynane, M. J. S, Waterworth, L. G. and Worrall, I. J., J. Organometal. Chem., 43, 1972).

U.S. Pat. No. 5,663,390 relates to the preparation of alkyl metal chlorides by reaction of an alkyl chloride with elemental metal in the presence of $H_2$ as reaction accelerator. The latter, however, is disadvantageous; more particularly, the process described is very complex and the conversion is only incomplete. At the same time, the aim of U.S. Pat. No. 5,663,390 is the preparation of dimethylindium chloride or methylindium dichloride, depending on the reaction time. Either pure dimethylindium chloride or pure methylindium dichloride is obtained as the reaction product and potential precursor starting material. The reaction overall is very inconvenient and costly, and is therefore unsuitable for the industrial scale.

Problem

The problem addressed by the present invention is that of providing a process which enables inexpensive preparation, in accordance with demand, of suitable precursor starting materials for indium-containing precursors, combined with a simple and rapid process regime. The process is also to enable the preparation of such compounds with high yield and high purity. The precursor starting materials should additionally be isolable in a simple manner and have sufficient storage stability.

In addition, indium-containing precursors obtainable from the starting material are to be very substantially free of oxygen impurities, and are to be obtainable in high yield and with high selectivity and purity proceeding from the starting material. As a result, the indium-containing precursors obtainable are to be particularly suitable for MOCVD processes, which requires high-purity organometallic compounds in each case for the production of semiconductor layers.

The process is additionally to be performable with a low level of environmental pollution and with low resource intensity.

Solution

The problem addressed by the present invention is solved by the subject-matter of the claims and the brief description of the invention which follows.

BRIEF DESCRIPTION OF THE INVENTION

1. Process for preparing a compound (A) of the general formula:

$$R_2InCl$$

comprising the reaction steps of
a1) reacting an indium donor with an alkyl donor to form the compound (A), the alkyl donor being alkylaluminium sesquichloride ($R_3Al_2Cl_3$), and the indium donor being indium trichloride ($InCl_3$),
a2) and optionally isolating compound (A) from the reaction mixture;
2. where R is an alkyl radical having 1 to 4 carbon atoms. The alkyl radical may be branched or unbranched, preferably unbranched. Process according to one of the preceding items, where R is methyl or ethyl.
3. Process according to one of the preceding items, where R is methyl.
4. Process according to one of the preceding items, wherein an auxiliary base is also added in reaction step a1), the auxiliary base comprising at least one halide of a metal of groups 1, 2 or 13 (IA, IIA or IIIA) of the Periodic Table.
5. Process according to item 4, wherein the auxiliary base comprises sodium chloride, potassium chloride, aluminium chloride or mixtures thereof.
6. Process according to item 4, wherein the auxiliary base is a mixture of sodium chloride and potassium chloride, and wherein the molar ratio of sodium chloride to potassium chloride is between 6:3 and 8:3.
7. Process according to item 4 or 5, wherein the auxiliary base is a mixture of aluminium chloride, sodium chloride and potassium chloride, and wherein the molar ratio of aluminium chloride to sodium chloride to potassium chloride is 45 to 55:30 to 40:10 to 20.
8. Process according to any of items 4 to 7, wherein 0.8 to 2.5 equivalents of auxiliary base are used per equivalent of indium donor in reaction step a1).
9. Process according to at least one of the preceding items, wherein between 0.6 and 2 equivalents of alkyl donor are used per equivalent of indium donor in reaction step a1).

10. Process according to at least one of the preceding items, wherein the indium donor in reaction step a1) is initially charged in the reaction vessel and then the alkyl donor is added.
11. Process according to item 10, wherein a mixture comprising indium donor and an auxiliary base is initially charged in reaction step a1) and then alkyl donor is added to this mixture, said auxiliary base comprising at least one halide of a metal of groups 1, 2 or 13 (IA, IIA or IIIA) of the Periodic Table.
12. Process according to any of the preceding items, wherein the process comprises the isolation of compound (A) as step a2), and wherein the isolation comprises the separation of volatile constituents from the reaction mixture present in the reaction vessel and the sublimation of compound (A) from the reaction mixture.
13. Process according to any of the preceding items, wherein reaction step a1) is performed in the absence of organic solvents.
14. Process according to any of items 1 to 13, wherein the yield of compound (A) is at least 79%.
15. Process according to any of items 1 to 14, wherein the purity of compound (A) is at least 95%.
16. Process for preparing trialkylindium of the formula $R_3In$, comprising the following reaction steps:
preparing dialkylindium chloride, compound (A), of the formula $R_2InCl$;
b1) reacting compound (A) with an alkyllithium to form lithium tetraalkylindate ($LiInR_4$), and isolating $LiInR_4$ from the reaction mixture, and
b2) reacting $LiInR_4$ with an indium chloride component to obtain a compound (B) of the general formula:

$$R_3In$$

where R is as defined in item 1, 2 or 3.
17. Process according to item 16, wherein the indium chloride component has the general formula:

$$R_aIn_bCl_c$$

where a is a number selected from 0, 1, 2 and 3 and b is a number selected from 1 and 2 and c is a number selected from 1, 2 and 3, and where a+b+c=4 or is a multiple of 4, and where R is as defined in item 1, 2 or 3.
18. Process according to either of items 16 and 17, wherein the indium chloride component is selected from $R_2InCl$, $R_3In_2Cl_3$, $RInCl_2$ and $InCl_3$.
19. Process according to any of items 16 to 18, wherein the yield of compound (B) is more than 90%.
20. Process according to any of items 16 to 19, wherein the purity of compound (B) is at least 99%.
21. Process according to any of items 1 to 15, comprising the following additional reaction steps:
c) reacting compound (A) with an alkylating agent to form compound (C) having the general formula:

$$R_2InR'$$

where R' is a nucleophilic radical selected from the group consisting of branched, unbranched, substituted or unsubstituted alkyl, substituted or unsubstituted aryl, and where R is as defined above.
22. Process according to item 21, wherein the alkylating agent is selected from R'MgX, R'Li and $R'_3Al$.
23. Process according to either of items 21 and 22, where R is methyl, and where R' is an $Me_2N$—$(CH_2)_3$— radical.
24. Use of the compound (A) according to item 1 for preparing compound (B) according to item 16.

25. Use of the compound (A) according to item 1 for preparing compound (C) according to item 21.

26. Use of the compound (B) prepared by a process according to any of items 16 to 20 as a precursor for metal-organic chemical vapour deposition (MOCVD) or metal-organic vapour phase epitaxy (MOVPE).

27. Use of the compound (C) prepared by a process according to any of items 21 to 23 as a precursor for metal-organic chemical vapour deposition (MOCVD) or metal-organic vapour phase epitaxy (MOVPE).

28. Compound (A) prepared by a process according to any of items 1 to 15.

29. Compound (B) prepared by a process according to any of items 16 to 20.

30. Compound (C) prepared by a process according to any of items 21 to 23.

31. Process according to any of the above items 1 to 15, comprising the following additional reaction steps:
  b1) reacting compound (A) with an alkyllithium to form lithium tetraalkylindate (LiInR$_4$), and isolating LiInR$_4$ from the reaction mixture, and
  b2) reacting LiInR$_4$ with an indium chloride component to obtain a compound (B) of the general formula:

$R_3In$ where R is as defined in item 1, 2 or 3.

DETAILED DESCRIPTION OF THE INVENTION

The problem is especially solved by a novel process for preparing dialkylindium chloride (compound of the formula (A)) having the general formula:

$R_2InCl$ where R is a lower alkyl radical, i.e. one having 1 to 4 carbon atoms. The alkyl radical may be branched or unbranched, preferably unbranched. Suitable alkyl radicals are therefore isopropyl, cyclopropyl, isobutyl, sec-butyl, tert-butyl, but in particular propyl, n-butyl and ethyl or methyl.

Because of the starting substances and further reagents used, the process is inexpensive and causes a low level of environmental pollution, and enables the preparation of $R_2InCl$ with a rapid process regime and high yield, and with high purity. More particularly, it is possible in accordance with the invention to substantially dispense with the use of organic solvents that are typically required, which contributes to a cost-effective and environmentally responsible process regime. It is additionally advantageous that compound (A) is isolable in a simple manner. This precursor starting material is likewise regularly nonpyrophoric and nonvolatile and has sufficient storage stability.

The process according invention is particularly suitable for preparing dimethylindium chloride (Me$_2$InCl) and diethylindium chloride (Et$_2$InCl), very particularly for the preparation of Me$_2$InCl. R is thus preferably selected from ethyl and methyl; most preferably, R is methyl.

First of all, the invention thus provides a novel process for preparing $R_2InCl$, i.e. the compound (A). The process according to the invention may be followed by further reaction steps, such that indium-containing precursors for MOCVD or MOVPE processes are also obtainable in accordance with the invention inexpensively and with a rapid process regime, and in high yield and purity. The process according to the invention thus comprises the preparation of compound (A). In embodiments, the process according invention may be followed by additional reaction steps for preparation of indium-containing precursors.

Inventive indium-containing precursors are preferably selected from compounds of the general formula $R_3In$ (compound (B)) and $R_2InR'$ (compound (C)).

According to the invention, indium-containing precursors of the general formula:

$R_3In$, are those in which R is a lower alkyl radical having 1 to 4 carbon atoms. The alkyl radical may be branched or unbranched, preferably unbranched. R is especially selected from ethyl and methyl; in particular, R is methyl. According to the invention, indium-containing precursors of the general formula:

$R_2InR'$, are those in which R is a lower alkyl radical having 1 to 4 carbon atoms, which may be branched or unbranched, and where R' is a nucleophilic radical other than R. R' is preferably selected from branched or unbranched and substituted or unsubstituted alkyl, branched or unbranched and substituted or unsubstituted aryl. R' may especially be phenyl or alkyl substituted by branched or unbranched alkyl or alkoxy groups, or by amine radicals.

More particularly, R' comprises alkyl or aryl radicals having 1 to 6 carbon atoms which are substituted by branched or unbranched alkyl or alkoxy groups such as methyl, ethyl, n-butyl, propyl, sec-butyl, tert-butyl, isobutyl, isopropyl, cyclopropyl, cyclobutyl, methoxy, ethoxy, n-butoxy, propoxy, sec-butoxy, tert-butoxy, isobutoxy, isopropoxy, cyclopropoxy, cyclobutoxy; or else R' comprises alkyl or aryl radicals having 1 to 6 carbon atoms which are substituted (especially monosubstituted, or disubstituted) by amine radicals which are themselves substituted by branched or unbranched alkyl groups, such as methyl, ethyl, n-butyl, propyl, sec-butyl, tert-butyl, isobutyl, isopropyl, cyclopropyl, cyclobutyl. R' may, for example, be phenyl, tolyl, mesityl, dimethylamino, diethylamino, dibutylamino, diisopropylamino, Et$_2$N—(CH$_2$)$_3$, Me$_2$N—(CH$_2$)$_2$, Me$_2$N—CH$_2$, Et$_2$N—(CH$_2$)$_2$, Et$_2$N—CH$_2$, isopropyl, cyclopropyl, isobutyl, sec-butyl, tert-butyl, cyclopropyl, but especially propyl, n-butyl and ethyl or methyl. If the definitions of R and R' encompass the same radicals, R and R' must be different from one another in compound (C). Thus, if R is methyl, R' must be different from methyl.

In one embodiment of the invention, R is methyl or ethyl and R' is an Me$_2$N—(CH$_2$)$_3$ radical. In a further embodiment of the invention, R is methyl and R' is ethyl. In a further embodiment of the invention, R is ethyl and R' is methyl. Therefore, the compounds that arise are Me$_2$InEt, Et$_2$InMe and Me$_2$In—(CH$_2$)$_3$—N—Me$_2$ or (CH$_3$)$_2$In—(CH$_2$)$_3$—N—(CH$_3$)$_2$.

In embodiments, further reaction steps thus follow the process according to the invention, and so indium-containing precursors, preferably $R_3In$ (i.e. compound (B)) or $R_2InR'$ (i.e. compound (C)), can be obtained inexpensively and in accordance with demand, and with a rapid process regime.

The indium-containing precursors (B) and (C) obtainable with preference from compound (A), because of their particularly high purity, are particularly suitable for the production of indium-containing films, such as InP, InAlP and AlInGaP films, in the semiconductor industry and in the related electronics industry, in the context of MOCVD or MOVPE processes.

1. Process for Preparing Compound (A)

The process according to the invention for preparing $R_2InCl$, i.e. compound (A), comprises the reaction steps of:
- a1) reacting an indium donor with an alkyl donor to form compound (A), the indium donor being indium trichloride ($InCl_3$) and the alkyl donor being alkylaluminium sesquichloride ($R_3Al_2Cl_3$), and
- a2) optionally isolating the compound (A).

Reaction Step a1):

According to the invention, the indium donor is a compound comprising indium. According to the invention, the indium donor is $InCl_3$.

According to the invention, the alkyl donor is a compound comprising an alkyl group, and the alkyl donor, according to the invention, is an alkyl chloride which thus also comprises at least one chlorine atom as well as the alkyl group. According to the invention, the alkyl donor is alkylaluminium sesquichloride ($R_3Al_2Cl_3$). $R_3Al_2Cl_3$ can also be prepared as a mixture of $R_2AlCl$ and $RAlCl_2$, which is also encompassed by the invention. Most preferably, the alkyl donor is selected from methylaluminium sesquichloride ($Me_3Al_2Cl_3$) and ethylaluminium sesquichloride ($Et_3Al_2Cl_3$), the alkyl donor further preferably being methylaluminium sesquichloride ($Me_3Al_2Cl_3$).

Preferably, for this reaction, 0.4 to 5 equivalents of alkyl donor are used per equivalent of indium donor. Further preferably 0.5 to 4.5 equivalents and especially preferably 0.6 to 4 equivalents of alkyl donor are used per equivalent of indium donor. If the alkyl donor is used in too low a proportion in relation to the indium donor, there is the risk of incomplete conversion and a reduced yield of compound (A). If excessively high amounts of alkyl donor are used in relation to the indium donor, the process becomes too expensive and too uneconomic overall, and is no longer performable in an economically viable manner on the industrial scale, which is undesirable in accordance with the invention.

It has been found to be particularly advantageous to use between 0.6 and 2 equivalents of alkyl donor per equivalent of indium donor, even further preferably between 0.8 and 1.3 equivalents of alkyl donor per equivalent of indium donor and most preferably between 0.9 and 1.1 equivalents of alkyl donor per equivalent of indium donor. In this way, it was surprisingly possible to achieve particularly advantageous yields of compound (A).

The reaction can take place in the presence of an auxiliary base. According to the invention, the auxiliary base comprises at least one metal halide. A metal halide preferred in accordance with the invention has the general formula:

$MX_n$ where n may assume the values of 1, 2 or 3, X is selected from chlorine, bromine, fluorine and iodine, and M is selected from the group of the IA metals, IIA metals and IIIA metals. Preferred group IA metals are potassium, sodium, lithium, rubidium and caesium. Preferred group IIA metals are magnesium, calcium, strontium and barium. A preferred group IIIA metal is aluminium. Preferably, M is a group IA and/or group IIIA metal. More preferably, M is sodium, potassium and/or aluminium. X is preferably selected from fluorine and chlorine. Further preferably, X is chlorine.

The use of an auxiliary base is advantageous. Thus, a eutectic salt melt can form in the process, which can contribute to compound (A) being obtained with high selectivity, and to any by-products, such as alkylindium dichloride ($RInCl_2$), forming only in traces.

In preferred embodiments, the auxiliary base comprises sodium chloride, potassium chloride, aluminium chloride or mixtures thereof. More particularly, the auxiliary base may be a mixture of sodium chloride, potassium chloride and aluminium chloride.

In a very particularly preferred embodiment, the auxiliary base is selected from potassium chloride, sodium chloride and mixtures thereof. These metal halides are available inexpensively and thus enable a particularly cost-effective process regime. More preferably, the auxiliary base comprises a mixture of potassium chloride and sodium chloride. It has been found that, surprisingly, such a mixture enables particularly high yields of compound (A). If only sodium chloride or only potassium chloride is used as auxiliary base, i.e. not a mixture, there may be a risk of reduced yields of compound (A).

Preferably, the molar ratio of sodium chloride to potassium chloride in the auxiliary base is between 6:4 and 8:2, further preferably between 6:3 and 8:3 and more preferably between 6.5:3 and 7.5:3. Surprisingly, observing such a molar ratio leads to particularly high yields of compound (A), in spite of the high sodium content. In a particularly preferred embodiment, the molar ratio of sodium chloride to potassium chloride in the auxiliary base is 7:3.

In embodiments in which the auxiliary base is a mixture of aluminium chloride, sodium chloride and potassium chloride, the molar ratio of aluminium chloride to sodium chloride to potassium chloride is preferably 45 to 55:30 to 40:10 to 20, more preferably 50:35:15.

The ratio of the equivalents of the auxiliary base used to the number of equivalents of the indium donor used is preferably 0.7:1 to 2.8:1, further preferably 0.8:1 to 2.5:1. Excessively high proportions of auxiliary base can reduce the yield through side reactions. In a particularly preferred embodiment, the ratio of the equivalents of the auxiliary base used to the number of equivalents of the indium donor used is between 1.8:1 and 2.2:1, even more preferably 2:1. This surprisingly enables the preparation of compound (A) with particularly high yield.

Preference is given to adding the indium donor and alkyl donor reactants successively to the reaction vessel. More preferably, a mixture comprising indium donor and optionally auxiliary base is first initially charged, and then the alkyl donor is added to this mixture. This surprisingly leads to high yields and additionally reduces the apparatus complexity. Thus, the indium donor and optionally the auxiliary base can simply be weighed into the reactor. Subsequently, the alkyl donor can be added in a controlled manner.

The alkyl donor can be added to the mixture of indium donor and optionally auxiliary base via a dropping funnel or an appropriate industrial embodiment, advantageously while stirring the initially charged indium donor and the optional auxiliary base. This contributes to ensuring sufficient mixing and quantitative conversion. In alternative embodiments, alkyl donor and optionally auxiliary base are initially charged in the reaction vessel and then indium donor is added.

Optionally, additional alkyl donor can be added during the reaction of alkyl donor and indium donor. This may be advantageous with regard to the yield of compound (A). However, in the inventive process regime, a sufficient yield is regularly achieved without addition of additional alkyl donor. Preferably in accordance with the invention, therefore, there is no addition of additional alkyl donor in reaction step a1) during the reaction.

The temperature during the addition of the alkyl donor is preferably below 100° C. More preferably, a temperature of 80° C. is not exceeded during the addition of the alkyl donor, in order to avoid unwanted side reactions. Cooling from the outside is possible in the course of addition of the alkyl donor. In the course of addition of the alkyl donor, the temperature preferably does not rise to higher than 50° C. and even more preferably not to higher than 35° C. This is advantageous in order to avoid the formation of by-products and for safety reasons and due to economic considerations.

After the alkyl donor has been added, the reaction mixture can optionally be heated. In the course of this, a temperature of 350° C., especially of 280° C., is not exceeded, in order to reduce the risk of side reactions. Advantageously, however, the temperature after addition of all the reactants and during the reaction is in the range from room temperature to 120° C., i.e., for example, below 80° C. or below 50° C. or below 40° C., in further embodiments below 35° C., or at room temperature, i.e. 25+/−5° C.

The alkyl donor is preferably added at standard pressure, i.e. 0.101325 MPa+/−5%, up to a slightly elevated pressure of up to 0.02 MPa. This may be followed by a vacuum step, preference thus being given to then applying vacuum with a residual gas pressure of preferably less than 1 hPa, more preferably less than 0.1 hPa and more preferably less than $5 \times 10^{-2}$ hPa.

Reaction step a1) preferably takes place under protective gas, more preferably under argon.

It was surprisingly possible by the process according to the invention to achieve high yields of compound (A) even in the absence of organic solvents. Preferably, no organic solvent is thus used in the reaction of the indium donor with the alkyl donor to form compound (A). Organic solvents are understood in accordance with the invention to mean carbonaceous, liquid substances. Absence of an organic solvent is understood in accordance with the invention to mean that no organic solvent is additionally used as reaction medium. This has the advantage that any possible organic contaminations in the compound (A) resulting from partial breakdown of the solvent are avoided. Furthermore, this allows the process to be conducted in a more environmentally responsible manner. Moreover, in the absence of organic solvents in step a1), a particularly high selectivity of the reaction was surprisingly recorded.

The reaction time in step a1) is preferably between 30 min and 30 hours. A reaction time between 30 min and 28 hours, especially between 2.5 hours and 25 hours, has been found to be particularly advantageous in relation to the yield of compound (A). Good results are being achieved with reaction temperatures in the range from about 90° C. to about 120° C., but also at temperatures below 35° C., or at room temperature, i.e. 25+/−5° C. A reaction time in step a1) of 3 to 8 hours, preferably 4 to 7 hours, may already be sufficient.

In a particularly preferred embodiment of the process according to the invention, the following reaction, in schematic form, proceeds in reaction step a1):

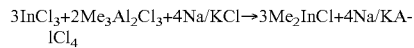

Reaction Step a2):

The isolation of compound (A), which is optional in accordance with the invention, preferably comprises the separation of volatile constituents from the reaction mixture present in the reaction vessel and/or process steps selected from the sublimation of the compound (A) from the reaction mixture and the mechanical removal of compound (A) from the reaction vessel. More preferably, the isolation of compound (A) comprises the separation of volatile constituents from the reaction mixture present in the reaction vessel and the sublimation of compound (A) from the reaction mixture.

According to the invention, the term "isolation" or "isolating" encompasses the separating of the particular desired reaction product from the reaction mixture present in the reaction vessel by removing the reaction product from the reaction vessel, or the removing of other compounds aside from the reaction product from the reaction mixture such that the reaction product remains in the reaction vessel.

The sublimation of the compound (A) is preferably effected by heating the reaction mixture to temperatures of up to 250° C., further preferably up to 220° C. and more preferably up to 200° C. The temperatures to which the reaction mixture is heated for sublimation of the compound (A) are preferably at least 90° C. and more preferably at least 95° C., and further preferably at least 100° C. Preferably, the temperature is maintained for at least 20 min, further preferably at least 40 min and more preferably at least 60 min for sufficient sublimation of the compound (A). In the course of sublimation of the compound (A), a vacuum may be applied, especially with a residual gas pressure of less than 0.1 hPa or of less than $5 \times 10^{-2}$ hPa. Alternatively, the sublimation of the compound (A) is possible at standard pressure at temperatures in the range from 150° C. to 200° C.

It has been found to be particularly advantageous for the purity of the compound (A) first to remove volatile by-products by applying a vacuum with a residual gas pressure of less than 0.1 hPa, preferably less than $5 \times 10^{-2}$ hPa, and only then to sublime the compound (A). Optionally, the isolation of the compound (A) may be followed by further steps to purify the compound (A), suitable processes for purifying chemical substances being known to those skilled in the art. Preferably in accordance with the invention, through the particular process regime and reactants, however, a sufficiently high purity of the compound (A) is achieved even without further purification steps. Preferably in accordance with the invention, therefore, aside from the isolation of compound (A), no further steps to purify the compound (A) are required.

In alternative embodiments, compound (A) is not isolated from the reaction mixture. In such embodiments, the reaction mixture comprising compound (A) and optionally the auxiliary base or the salt melt that results when an auxiliary base is used is used directly for preparation of indium-containing precursors, especially compound (B) or (C). In these embodiments, additional reaction steps for preparation of preferably compound (B) or (C) thus directly follow on from reaction step a1) without an isolation of compound (A) from the reaction mixture, i.e. without the reaction step a2). This enables an even more rapid process regime in the preparation of indium-containing precursors.

The process according to the invention enables the preparation of compound (A) with a yield of preferably at least 70%, further preferably at least 75%, even further preferably at least 79% and very especially preferably of at least 85% and even more preferably more than 90% and even more preferably more than 95%. Yield figures given for the invention are always based on the theoretical yield.

The purity of the compound (A) prepared in accordance with the invention is preferably at least 95%, more preferably at least 98% and even more preferably more than 99%. Thus, preferably not more than 5%, more preferably not more than 2% and further preferably less than 1% of impurities, i.e. unwanted substances, are present in the compound (A) prepared.

A preferred compound (A) obtainable by the process according to the invention is selected from dimethylindium chloride ($Me_2InCl$) and diethylindium chloride ($Et_2InCl$). Most preferably, the process according to the invention is suitable for preparation of $Me_2InCl$.

2. Further Processing of the Compound (A) to Give Indium-Containing Precursors

The compound (A) obtained by the process described above can optionally be processed further to give indium-containing precursors, preferably selected in accordance with the invention from compounds (B) and (C). The invention therefore also includes the use of the compound (A) prepared by the process according to the invention for preparation of indium-containing precursors, preferably selected from compound (B) and (C), for MOCVD or MOVPE processes.

The compound (A) prepared in accordance with the invention is particularly suitable for preparation of indium-containing precursors of the general formula:

$$R_3In,$$

i.e. compound (B), where R is a lower alkyl radical having 1 to 4 carbon atoms. The alkyl radical may be branched or unbranched, preferably unbranched. R is preferably selected from ethyl and methyl; in particular, R is methyl.

Alternatively, the compound (A) prepared in accordance with the invention can be used to prepare indium-containing precursors of the general formula:

$$R_2InR',$$

i.e. compound (C), where R is a lower alkyl radical having 1 to 4 carbon atoms, which may be branched or unbranched, and where R' is a nucleophilic radical other than R.

R' is preferably selected from branched or unbranched and substituted or unsubstituted alkyl, branched or unbranched and substituted or unsubstituted aryl. R' may especially be phenyl or alkyl substituted by branched or unbranched alkyl or alkoxy groups, or by amine radicals.

More particularly, R' comprises alkyl or aryl radicals having 1 to 6 carbon atoms which are substituted by branched or unbranched alkyl or alkoxy groups such as methyl, ethyl, n-butyl, propyl, sec-butyl, tert-butyl, isobutyl, isopropyl, cyclopropyl, cyclobutyl, methoxy, ethoxy, n-butoxy, propoxy, sec-butoxy, tert-butoxy, isobutoxy, isopropoxy, cyclopropoxy, cyclobutoxy;

or else R' comprises alkyl or aryl radicals having 1 to 6 carbon atoms which are substituted (especially monosubstituted, or disubstituted) by amine radicals which are themselves substituted by branched or unbranched alkyl groups, such as methyl, ethyl, n-butyl, propyl, sec-butyl, tert-butyl, isobutyl, isopropyl, cyclopropyl, cyclobutyl. R' may, for example, be phenyl, tolyl, mesityl, dimethylamino, diethylamino, dibutylamino, diisopropylamino, $Et_2N-(CH_2)_3$, $Me_2N-(CH_2)_2$, $Me_2N-CH_2$, $Et_2N-(CH_2)_2$, $Et_2N-CH_2$, isopropyl, cyclopropyl, isobutyl, sec-butyl, tert-butyl, cyclopropyl, but especially propyl, n-butyl and ethyl or methyl. If the definitions of R and R' encompass the same radicals, R and R' must be different from one another in compound (C). Thus, if R is methyl, R' must be different from methyl.

In one embodiment of the invention, R is methyl or ethyl and R' is an $Me_2N-(CH_2)_3$ radical. In a further embodiment of the invention, R is methyl and R' is ethyl. In a further embodiment of the invention, R is ethyl and R' is methyl. Therefore, the compounds that arise are $Me_2InEt$, $Et_2InMe$ and $Me_2In-(CH_2)_3-N-Me_2$ or $(CH_3)_2In-(CH_2)_3-N-(CH_3)_2$.

2.1. Further Processing of Compound (A) to Give Compound (B)

In preferred embodiments, the preparation of compound (A) is additionally followed by the following further reaction steps by which compound (B) is obtainable:

b1) reacting compound (A) with an alkyllithium to form lithium tetraalkylindate, and isolating $LiInR_4$ from the reaction mixture, and b2) reacting the $LiInR_4$ with an indium chloride component to obtain compound (B).

Reaction step b2) may directly follow on from reaction step b1). Alternatively, reaction step b2) may also be effected with a time offset from reaction step b1).

Reaction Step b1):

Reaction step b1) comprises the reaction of compound (A) with an alkyllithium to form lithium tetraalkylindate, the lithium tetraalkylindate satisfying the following general formula:

$$LiInR_4$$

where R is as defined above. R is preferably methyl or ethyl, even more preferably methyl.

The term "alkyllithium" encompasses those compounds which comprise at least one alkyl group and lithium. According to the invention, the alkyllithium preferably has the following general formula:

$$RLi$$

where R is as defined above. Most preferably, the alkyllithium is selected from ethyllithium (EtLi) and methyllithium (MeLi); the alkyllithium is further preferably MeLi. In this way, it is also possible to obtain compounds of the formula (C), $R_2InR'$, when an alkyllithium of the formula R'Li where R' is different from R and is as defined above is used. Otherwise, RLi and R'Li are from the same substance class.

According to the invention, the alkylating agent used in reaction step b1) is alkyllithium. The person skilled in the art is aware of further alkylating agents which can be used for alkylation reactions. Further organometallic alkylating agents are known and may include organic compounds of metals of groups 1, 2, 12 and 13, i.e., for example, of alkali metals and alkaline earth metals. Of especially good suitability are lithium, magnesium and sodium, but also elements such as zinc and aluminium. Alkylating agents known to those skilled in the art include especially dimethylzinc or trimethylaluminium.

Suitable organic solvents for step b1) are especially dialkyl ethers. Very particular preference is given to using a solvent selected from diethyl ether, longer-chain ethers and mixtures thereof in reaction step b1), longer-chain ethers being those comprising alkyl groups having more than 2 carbon atoms. Even more preferably, the solvent is diethyl ether or di-n-butyl ether, further preferably diethyl ether.

Preferably, in reaction step b1), 1 to 5.6 equivalents of alkyllithium are used per equivalent of compound (A), more preferably 1.2 to 5.4 equivalents of alkyllithium per equivalent of compound (A). It has been found to be particularly advantageous not to use too much alkyllithium. Thus, the process overall is performable in an even more cost-effective manner, and it was possible to achieve a high purity and yield of $LiInR_4$. More particularly, not more than 6 equivalents of alkyllithium should be used per equivalent of $R_2InCl$, i.e. compound (A), in order that the process is performable in a cost-effective manner and any contaminations by alkyllithium in the $LiInR_4$ are reduced or prevented. However, not too little alkyllithium based on compound (A) should be used either, otherwise there will be inadequate conversion and the yield of $LiInR_4$ may be reduced. It has been found to be particularly advantageous to use between 1.3 and 3 equivalents of alkyllithium per equivalent of $R_2InCl$, more preferably between 1.5 and 2.5 equivalents and even more preferably between 1.8 and 2.2 equivalents, and most preferably about 2 equivalents.

In preferred embodiments, the alkyllithium is initially charged in the organic solvent and then compound (A) is added, preferably at temperatures between −10 and 10° C., further preferably at temperatures between −5 and 5° C., further preferably at −2 to 2° C. and even more preferably at 0+/−1° C. The reaction preferably takes place at temperatures between −30° C. and the boiling point of the organic solvent, further preferably at −5° C. to 35° C.

In alternative embodiments, compound (A) is initially charged in the organic solvent and the alkyllithium is subsequently added. This preferably involves adding the alkyllithium dropwise as a mixture with the organic solvent, more preferably at temperatures between −5 and 5° C., further preferably at −2 to 2° C.

After all the reactants have been added, preference is given to stirring for preferably at least 10 min, further preferably at least 15 min. The reaction time is generally not more than 48 hours, preferably not more than 24 hours.

$LiInR_4$ is isolated from the reaction mixture. This is preferably done by removing the solvent and any by-products, especially LiCl, or residues of the reactants, preferably by distilling off volatile constituents and/or filtering the reaction mixture. Isolation of the $LiInR_4$ by filtration and subsequent distillation of the solvent has been found to be particularly advantageous. Further purifying steps may follow, by processes known to those skilled in the art for purifying chemical substances.

In a preferred embodiment, the following reaction, in schematic form, proceeds in reaction step b1):

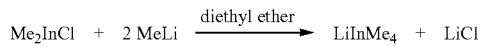

Reaction Step b2):

Compound (B) is preparable from $LiInR_4$ by reaction of $LiInR_4$ with an indium chloride component.

According to the invention, the "indium chloride component" is a compound comprising indium and chloride. The term "indium chloride component", more particularly, also encompasses compounds which also comprise at least one alkyl radical as well as indium and chloride. The indium chloride component preferably has the following general formula:

where a is a number selected from 0, 1, 2 and 3 and b is a number selected from 1 and 2 and c is a number selected from 1, 2 and 3, and where a+b+c=4 or is a multiple of 4; more preferably, the sum of a, b and c=4 or 8. R is as defined above.

Most preferably, the indium chloride component is selected from $InCl_3$, $R_2InCl$, $R_3In_2Cl_3$, $RInCl_2$ and mixtures thereof. Very particularly preferred indium chloride components are $R_2InCl$ or $R_3In_2Cl_3$, especially $Me_2InCl$, $Et_2InCl$, $Me_3In_2Cl_3$ or $Et_3In_2Cl_3$, further preferably $Me_2InCl$ or $Me_3In_2Cl_3$. It is thus also possible in accordance with the invention to use compound (A) as the indium chloride component, which makes the process according to the invention even less expensive. In particularly preferred embodiments, the indium chloride component is therefore $R_2InCl$.

The molar ratio of lithium tetraalkylindate to the indium chloride component may be between 1:1 and 3:1, preferably about 1:1, 2:1 or 3:1. In embodiments in which the indium chloride component is $R_2InCl$, a molar ratio of lithium tetraalkylindate to the indium chloride component of about 1:1 has been found to be particularly advantageous. In embodiments in which the indium chloride component is $R_3In_2Cl_3$, a molar ratio of lithium tetraalkylindate to the indium chloride component of about 3:1 is particularly advantageous. In embodiments in which the indium chloride component is $RInCl_2$, a molar ratio of lithium tetraalkylindate to the indium chloride component of about 2:1 is particularly advantageous.

The reaction of lithium tetraalkylindate with the indium chloride component can be effected in an organic solvent. Suitable organic solvents for step b2) are selected from alkanes including cyclic saturated hydrocarbons, aromatics, alcohols, ethers and cyclic ethers. Suitable organic solvents for step b2) have been found to be especially alkanes and aromatics, preferably selected from n-pentane, cyclohexane, n-decane, n-heptane, n-hexane, methylcyclohexane, n-nonane, n-octane and benzene, very particular preference being given to n-pentane.

In alternative embodiments, no organic solvent is used in reaction step b2), i.e. no organic solvent is used additionally as reaction medium. This has the advantage that any possible organic contaminations which restrict usability in compound (B) that result from partial breakdown of the solvent are avoided. Furthermore, this allows the process to be conducted in a more environmentally responsible manner. In one embodiment, step b2) is therefore performed in the absence of organic solvents.

Preferably, the $LiInR_4$ is initially charged together with the indium chloride component and optionally the auxiliary base. Subsequently, the organic solvent can be added. This is preferably followed by heating, preferably to temperatures between 30° C. and 120° C., further preferably to temperatures between 40° C. and 100° C. and even more preferably to temperatures between 50° C. and 90° C. Preference is given to maintaining such a temperature for at least 10 min and at most 24 hours, preferably for at least 30 min and at most 20 hours, further preferably at least 40 min and at most 12 hours and even more preferably for at least 90 min and at most 3 hours.

Subsequently, preference is given to cooling, preferably to a temperature of 25+/−5° C.

Preferably, compound (B) is then isolated from the mixture. The isolating of compound (B) preferably comprises the removing of the organic solvent and of compound (B) from the reaction mixture which may comprise LiCl. This is especially effected by recondensation of organic solvent and compound (B) into a new vessel. Subsequently, the solvent is separated from compound (B), preferably by distilling it off under reduced pressure with preferably a residual gas pressure of less than 0.1 hPa, further preferably not more than 0.01 hPa, preferably into a cold trap at preferably −10° C.+/−5° C. Compound (B) preferably remains in the vessel. Optionally, further purifying steps may follow, by purifying processes known to those skilled in the art. More preferably, the further purifying steps include the sublimation of compound (B).

In a preferred embodiment, the following reaction, in schematic form, proceeds in reaction step b2):

In an alternative embodiment, the following reaction, in schematic form, proceeds in reaction step b2):

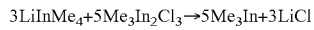

The additional reaction steps comprising b1) and b2) enable the preparation of compound (B) from compound (A) with a yield of preferably at least 60%, further preferably at least 70%, even further preferably at least 75% and very especially preferably of 85% and even further preferably more than 90%. The purity of the compound (B) prepared in accordance with the invention is preferably at least 99%, more preferably at least 99.5% and more preferably more than 99.8%, and further preferably more than 99.999%. Especially in the case of performance of a further step for purifying the compound (B) prepared, preferably by sublimation of compound (B), a purity of >99.999% can be achieved.

2.2. Further Processing of Compound (A) to Give Compound (C)

In alternative embodiments, compound (A) is processed further to give compound (C), by adding additional further reaction steps onto the process according to the invention, comprising:

c) reacting compound (A) with an alkylating agent to form compound (C).

As described above, compound (C) is a compound of the general formula $R_2InR'$ where R and R' are each as defined above.

More preferably, compound (C) is dimethylaminopropyldimethylindium (DADI), dimethylethylindium or diethylmethylindium.

The alkylating agent in step c) is especially selected from R'MgX, R'Li and R'$_3$Al. More preferably, the alkylating agent is $Me_2N$—$(CH_2)_3$-M where M is especially MgCl or Li.

The conversion of compound (A) to $R_2InR'$, for example DADI, can be effected in an organic solvent by reaction with the alkylating agent, for example $Me_2N$—$(CH_2)_3$-M in the case of DADI. The organic solvent may be a dialkyl ether or a cyclic ether or mixtures thereof, especially dioxane, diethyl ether, dibutyl ether, tert-butyl ethyl ether (ETBE), 2-methoxy-2-methylpropane (methyl tert-butyl ether, MTBE) or tetrahydrofuran. Other suitable solvents are aliphatic or aromatic hydrocarbons, especially aliphatic or aromatic hydrocarbons having five to nine carbon atoms, which may be linear or cyclic, and mixtures thereof, for example n-pentane, isopentane, neopentane, cyclopentane, methylcyclopentane, n-hexane, 2-methylpentane, 3-methylpentane, 2,2-dimethylbutane, 2,3-dimethylbutane, cyclohexane, methylcyclohexane, heptane, octane, petroleum ether or toluene. Good results can especially be achieved with tetrahydrofuran (THF), diethyl ether, pentane or else cyclohexane.

Reaction step c) is typically effected under protective gas.

In one embodiment of the invention, the alkylating agent is initially charged and then compound (A) is added. In an alternative embodiment, it is also possible for compound (A) to be initially charged, followed by addition of the alkylating agent. Both compound (A) and the alkylating agent can advantageously be used dissolved in a solvent. This procedure gives good results especially when alkyllithium or alkylmagnesium halides are used (R'Li, R'MgX). R'$_3$Al can also be used without solvent.

In that case—according to the embodiment—either the solution of compound (A) or the alkylating agent, optionally as a solution, is added dropwise.

In that case, compound (A) can be added dropwise as a mixture with one of the abovementioned solvents, but advantageously especially as a mixture with a combination of these organic solvents, especially in a mixture with tetrahydrofuran (THF), diethyl ether, pentane and combinations thereof.

The dropwise addition of compound (A) is preferably effected gradually, more preferably over the course of at least 10 min, further preferably over the course of at least 20 min. The addition of compound (A) is effected preferably at a temperature below 50° C., further preferably below 40° C. and more preferably at room temperature, i.e. 25° C.+/−5° C.

After all the reactants have been added, especially alkylating agent and compound (A), the reaction is effected, which can be conducted while stirring. Preferably, the temperature during the reaction (stirring) is less than 50° C., further preferably below 40° C. and more preferably room temperature, i.e. 25° C.+/−5° C. Preference is given to stirring for at least 5 hours, further preferably for at least 10 hours. For reasons of cost, reaction times of 80 hours, further preferably 50 hours, are usually not exceeded.

Subsequently, compound (C) is preferably isolated from the reaction mixture. The isolating of compound (C) may comprise the removal of the organic solvent, preferably under reduced pressure, and the separation of compound (B) from the reaction mixture by filtration and/or distillation.

The alkylating agents can be prepared by known processes, for example $Me_2N$—$(CH_2)_3$-M from 3-chloro-1-(dimethylamino)propane by reaction with magnesium turnings or lithium turnings. Typically, $Me_2N$—$(CH_2)_3$-M is prepared in an organic solvent, especially THF, while supplying heat. Optionally, iodine can be added for activation.

By maintaining the conditions of the above-described preparation process according to the invention for preparing compound (A) and optionally of the further processing to give indium-containing precursors, preferably selected from compounds (B) and (C), these compounds can be prepared in high yield and with high purity. The invention additionally includes the compound (A) prepared by the process, especially $Me_2InCl$, and the indium-containing precursors obtainable therefrom, especially trimethylindium, dimethylaminopropyldimethylindium and dimethylethylindium.

Especially the high yield and purity, and also cost-effective and comparatively environmentally benign process selection, in the process according to the invention makes the process ideally suited to the industrial preparation of compound (A) or indium-containing precursors. More particularly, no pyrophoric intermediates form in accordance with the invention, which is particularly advantageous in the light of cost-effective and low-complexity preparation. The process according to the invention is especially characterized by particularly high indium exploitation. The overall indium conversion in the process according to the invention, based on the indium donor used, is preferably ≥70%, further preferably ≥75%, more preferably 80% and even more preferably >95%. The oxygen content in the compound (B) or (C) optionally obtainable, including indium peroxides and oxides, is preferably <100 ppm (m/m), especially even <1 ppm (m/m).

The indium-containing precursors optionally preparable by the process according to the invention, especially trimethylindium and dimethyl-aminopropyldimethylindium, because of their excellent purity, especially their very low oxygen content, are particularly suitable for MOCVD or MOVPE processes, for example for production of semiconductors or semiconductor components. The semiconductors or semiconductor components ultimately produced have various possible industrial uses. The invention therefore also includes the use of the compounds (B) and/or (C) optionally preparable in accordance with the invention as precursors for metal-organic chemical vapour deposition (MOCVD) or metal-organic vapour phase epitaxy (MOVPE).

WORKING EXAMPLES $Me_2InCl$ was prepared by the process according to the invention. Compound (A) was also used to prepare $Me_3In$ as compound (B) or dimethylaminopropyldimethylindium as compound (C).

1. Preparation of $Me_2InCl$
   1.1. Reaction of Indium Trichloride with Methylaluminium Sesquichloride to form $Me_2InCl$ (Equivalents of Auxiliary Base to Equivalents of Indium Donor 2:1)

A 100 ml three-neck flask with a short Liebig condenser and two PTFE valves was initially charged under argon with 10 g (45.2 mmol) of $InCl_3$, 3.70 g (63.3 mmol, 1.4 equiv. based on $InCl_3$) of NaCl and 2.02 g (27.1 mmol, 0.6 equiv.) of KCl, which were mixed thoroughly. A dropping funnel under argon was used to add 9.29 g (45.2 mmol, 1 equiv.) of $Me_3Al_2Cl_3$ dropwise to the salt mixture. The reaction proceeded with slight exothermicity, not exceeding a temperature of 30° C. On completion of addition, the reaction mixture formed was stirred for 20 hours overnight. In the course of this, the mixture thickened to become a virtually unstirrable mass. Subsequently, the apparatus was placed under high vacuum ($1 \times 10^{-2}$ to $1 \times 10^{-3}$ hPa) at room temperature, and residual volatile methylaluminium compounds were distilled into a liquid nitrogen-cooled Schlenk flask for 0.5 hour. After the distillation had ended, the condenser was cooled to 30° C. and the reaction mixture was heated to 120° C. for two hours. In the course of this, $Me_2InCl$ sublimed out of the reaction mixture. 7.99 g (44.3 mmol) of $Me_2InCl$ (identified by NMR) were obtained. This corresponds to a yield of 98.3%.

1.2. Reaction of Indium Trichloride with Methylaluminium Sesquichloride to Form $Me_2InCl$ (Equivalents of Auxiliary Base to Equivalents of Indium Donor 1:1)

A 100 ml three-neck flask with a short Liebig condenser and two PTFE valves was initially charged under argon with 10 g (45.2 mmol) of $InCl_3$, 1.85 g (31.6 mmol, 0.7 equiv. based on $InCl_3$) of NaCl and 1.02 g (13.6 mmol, 0.3 equiv.) of KCl, which were mixed thoroughly. A dropping funnel under argon was used to add 9.26 g (45.2 mmol, 1 equiv.) of $Me_3Al_2Cl_3$ dropwise to the salt mixture. The reaction proceeded with slight exothermicity. On completion of addition, the reaction mixture formed was stirred for 20 hours overnight. In the course of this, the mixture thickened to become a virtually unstirrable mass. Subsequently, the apparatus was placed under high vacuum ($10^{-2}$ to $10^{-3}$ hPa) at room temperature, and residual volatile methylaluminium compounds were distilled into a liquid nitrogen-cooled Schlenk flask for one hour. After the distillation had ended, the condenser was cooled to 30° C. and the reaction mixture was heated to 120° C. for three hours. In the course of this, the desired product sublimed out of the reaction mixture. 6.46 g (35.9 mmol) of $Me_2InCl$ (identified by NMR) were obtained. This corresponds to a yield of 79.5%.

1.3. Reaction of Indium Trichloride with Methylaluminium Sesquichloride to Form $Me_2InCl$ (Equivalents of Auxiliary Base to Equivalents of Indium Donor 2:1)

A 100 ml three-neck flask with a short Liebig condenser and two PTFE valves was initially charged under argon with 10 g (45.2 mmol) of $InCl_3$ and 5.29 g (90.4 mmol, 2 equiv.) of NaCl, which were mixed thoroughly. A dropping funnel under argon was used to add 9.26 g (45.2 mmol, 1 equiv.) of $Me_3Al_2Cl_3$ dropwise to the salt mixture. The reaction proceeded with slight exothermicity. On completion of addition, the reaction mixture formed was stirred for 20 hours overnight, in the course of which the mixture thickened to become a virtually unstirrable mass. Subsequently, the apparatus was placed under high vacuum ($10^{-2}$ to $10^{-3}$ mbar) at room temperature, and residual volatile methylaluminium compounds were distilled into a liquid nitrogen-cooled Schlenk flask for 1.5 hours. After the distillation had ended, the condenser was cooled to 30° C. and the reaction mixture was heated to 120° C. for 1.5 hours, in the course of which the desired product sublimed out of the reaction mixture. 6.27 g (34.8 mmol) of $Me_2InCl$ (identified by NMR) were obtained. This corresponds to a yield of 76.9%.

1.4 Reaction of Indium Trichloride with Methylaluminium Sesquichloride to Form Me2InCl (Equivalents of Auxiliary Base to Equivalents of Indium Donor 2.3:1; in situ Preparation of Methylaluminium Sesquichloride)

1.22 g (45.2 mmol, 2 equiv.) of aluminium, 15.90 g (119.3 mmol, 5.3 equiv.) of aluminium trichloride and 7.15 g (113 mmol, 5 equiv.) of Na/KCl were initially charged in a Schlenk flask equipped with a sublimation finger, and the reaction mixture was heated to 130° C. until a clear melt had formed above the aluminium.

Subsequently, the reaction mixture was cooled down to 80° C., and chloromethane was introduced into the reaction mixture at this temperature under standard pressure. In total, the introduction of chloromethane was maintained at 80° C. while stirring for 16 hours.

Subsequently, 5.0 g (22.6 mmol) of indium trichloride and 3.29 g (52 mmol, 2.3 equiv.) of Na/KCl were added. Thereafter, the system was heated gradually up to 150-160° C. From about 150° C., the resublimation of a colourless solid on the sublimation finger was observed. 2.56 g (14.2 mmol, yield: 63%) $Me_2InCl$, identified via $^1H$ NMR, were obtained in coarse crystalline form.

2. Further Processing of $Me_2InCl$ to give $Me_3In$
   2.1. Reaction of $Me_2InCl$ with Alkyllithium to Form $LiInMe_4$ 1441 mg of $Me_2InCl$ (7.8 mmol) from Example 1.1 were added at 0° C. to 10 ml of a MeLi solution (1.565 mol/L in diethyl ether). The suspension was stirred at room temperature overnight and filtered. The clear filtrate was freed of the solvent, and 1079 mg of a colourless solid were isolated (corresponding to 5.9 mmol of $LiInMe_4$, 76%).

2.2. Reaction of $LiInMe_4$ with $Me_2InCl$ to form $Me_3In$ 1079 mg of $LiInMe_4$ (5.9 mmol, from Example 2.1) and 1067 mg of $Me_2InCl$ (5.9 mmol) were initially charged in a 125 ml Parr bomb, and 20 ml of pentane were added. Subsequently, the Parr bomb was immersed into an oil bath preheated to 70° C. and stirred at that temperature overnight. At 70° C., a slightly turbid suspension was observed, which solidified to become a crystal slurry as it cooled down to room temperature. The volatile constituents of the Parr bomb were recondensed in a cold trap (RT→−78° C.), and then the pentane solvent was removed at −8° C. (sodium chloride/ice mixture) under fine vacuum. 1591 mg of a colourless solid were isolated (10.0 mmol, yield: 81% trimethylindium).

3. Further Processing of Me$_2$InCl to Give Dimethylaminopropyl-Dimethylindium (DADI)

3.1. Reaction of Me$_2$InCl with Dimethylaminopropyl-magnesium Chloride

A 500 ml three-neck flask was initially charged with 75 ml of dried THF and 4.04 g (166.4 mmol, 3 equiv.) of magnesium turnings, and the contents were heated to reflux.

After adding a spatula-tip of iodine to activate the magnesium, 10.12 g (83.2 mmol, 1.5 equiv.) of 3-dimethylaminopropyl chloride were slowly added dropwise and then the reaction mixture was heated under reflux for a further 2.5 h. After the reaction mixture had cooled to room temperature, 10.00 g (55.4 mmol) of Me$_2$InCl from Example 1.1 dissolved in 75 ml of dried THF were added dropwise within 30 minutes, and the resulting reaction solution was stirred at room temperature for 20 hours.

Subsequently, the THF was removed under reduced pressure, the residue was suspended in 100 ml of dried pentane and stirred at room temperature for 2 h, and the resulting white solid was removed by means of a reversible frit and washed twice with 50 ml each time of dried pentane. The clear filtrate was concentrated to dryness under reduced pressure and distilled at 80° C. for purification. DADI was obtained as a clear liquid. Yield: 7.67 g (36.0 mmol), corresponding to 65%.

3.2. Reaction of Me$_2$InCl with 3-dimethylaminopropyl-lithium

A 500 ml three-neck flask was initially charged with 75 ml of dried THF and 1.16 g (170 mmol, 3 equiv.) of lithium turnings, and the contents were heated to reflux.

After attainment of reflux, 10.12 g (83.2 mmol, 1.5 equiv.) of 3-dimethylamino-propyl chloride were slowly added dropwise and then the reaction mixture was heated under reflux for a further 2.5 h. After the reaction mixture had cooled to room temperature, 10.00 g (55.4 mmol) of Me$_2$InCl from Example 1.2 dissolved in 75 ml of dried THF were added dropwise within 30 minutes, and the resulting reaction solution was stirred at room temperature for 20 hours.

Subsequently, the THF was removed under reduced pressure, the residue was suspended in 100 ml of dried pentane and stirred at room temperature for 2 h, and the resulting white solid was removed by means of a reversible frit and washed twice with 50 ml each time of dried pentane. The clear filtrate was concentrated to dryness under reduced pressure and distilled at 80° C. for purification. DADI was obtained as a clear liquid, yield: 7.7 g (36.6 mmol), corresponding to 66%.

The invention claimed is:

1. Process for preparing a compound (A) of the general formula:

$R_2InCl$ comprising the reaction steps of
a1) reacting an indium donor with an alkyl donor to form the compound (A), the alkyl donor being alkylaluminium sesquichloride ($R_3Al_2Cl_3$), and the indium donor being indium trichloride ($InCl_3$),
a2) and optionally isolating compound (A) from the reaction mixture;
where R is an alkyl radical having 1 to 4 carbon atoms, and where R is branched or unbranched.

2. Process according to claim 1, where R is methyl or ethyl.

3. Process according to claim 1, wherein an auxiliary base is also added in reaction step a1), the auxiliary base comprising at least one halide of a metal of groups 1, 2 or 13 (IA, IIA or IIIA) of the Periodic Table.

4. Process according to claim 3, wherein the auxiliary base comprises sodium chloride, potassium chloride, aluminium chloride or mixtures thereof.

5. Process according to claim 3, wherein the auxiliary base is a mixture of sodium chloride and potassium chloride, and wherein the molar ratio of sodium chloride to potassium chloride is between 6:3 and 8:3.

6. Process according to claim 3, wherein the auxiliary base is a mixture of aluminium chloride, sodium chloride and potassium chloride, and wherein the molar ratio of aluminium chloride to sodium chloride to potassium chloride is 45 to 55:30 to 40:10 to 20.

7. Process according to claim 3, wherein 0.8 to 2.5 equivalents of auxiliary base are used per equivalent of indium donor in reaction step a1).

8. Process according to claim 1, wherein between 0.6 and 2 equivalents of alkyl donor are used per equivalent of indium donor in reaction step a1).

9. Process according to claim 1, wherein the process comprises the isolation of compound (A) as step a2), and wherein the isolation comprises the separation of volatile constituents from the reaction mixture present in the reaction vessel and the sublimation of compound (A) from the reaction mixture.

10. Process for preparing trialkylindium of the formula R$_3$In, comprising the following reaction steps:
preparing dialkylindium chloride, compound (A), of the formula R$_2$InCl;
b1) reacting compound (A) with an alkyllithium to form lithium tetraalkylindate (LiInR$_4$), and isolating LiInR$_4$ from the reaction mixture, and
b2) reacting LiInR$_4$ with an indium chloride component to obtain a compound (B) of the general formula:

$R_3In$ where R is as defined in claim 1.

11. Process according to claim 10, wherein the indium chloride component has the general formula:

$R_aIn_bCl_c$ where a is a number selected from 0, 1, 2 and 3 and b is a number selected from 1 and 2 and c is a number selected from 1, 2 and 3, and where a+b+c=4 or is a multiple of 4, and where R is an alkyl radical having 1 to 4 carbon atoms, and where R is branched or unbranched.

12. Process according to claim 10, wherein the indium chloride component is selected from R$_2$InCl, R$_3$In$_2$Cl$_3$, RInCl$_2$ and InCl$_3$.

13. Process according to claim 1, comprising the following additional reaction steps:
c) reacting compound (A) with an alkylating agent to form compound (C) having the general formula:

$R_2InR'$ where R' is a nucleophilic radical selected from the group consisting of branched, unbranched, substituted or unsubstituted alkyl, substituted or unsubstituted aryl, and where R is an alkyl radical having 1 to 4 carbon atoms, and where R is branched or unbranched.

14. Process according to claim 13, wherein the alkylating agent is selected from R'MgX, R'Li and R'$_3$Al.

15. Process according to claim 13, where R is methyl, and where R' is an Me$_2$N—(CH$_2$)$_3$— radical.

16. A process for preparing compound (B), comprising:
reacting compound (A having the general formula: $R_2InCl$, where R is an alkyl radical having 1 to 4 carbon atoms, and where R is branched or unbranched, with an alkyllithium to form lithium tetraalkylindate ($LiInR_4$), isolating $LiInR_4$ from the reaction mixture, and
reacting $LiInR_4$ with an indium chloride component to obtain the compound (B) having the general formula: $R_3In$, where R is an alkyl radical having 1 to 4 carbon atoms, and where R is branched or unbranched.

17. A process for preparing compound (C), comprising:
reacting compound (A) having the general formula: $R_2InCl$, where R is an alkyl radical having 1 to 4 carbon atoms, and where R is branched or unbranched, with an alkylating agent to form the compound (C) having the general formula: $R_2InR'$, where R' is a nucleophilic radical selected from the group consisting of branched, unbranched, substituted or unsubstituted alkyl, substituted or unsubstituted aryl, and where R is an alkyl radical having 1 to 4 carbon atoms, and where R is branched or unbranched.

18. In a metal-organic chemical vapour deposition (MOCVD) or metal-organic vapour phase epitaxy (MOVPE), wherein the improvement comprises, utilizing a precursor of the compound (B) prepared by a process according to claim 10.

19. In a metal-organic chemical vapour deposition (MOCVD) or metal-organic vapour phase epitaxy (MOVPE), wherein the improvement comprises, utilizing the compound (C) prepared by a process according to claim 13.

20. Process according to claim 2, wherein an auxiliary base is also added in reaction step a1), the auxiliary base comprising at least one halide of a metal of groups 1, 2 or 13 (IA, IIA or IIIA) of the Periodic Table.

* * * * *